United States Patent [19]

Matson et al.

[11] Patent Number: 5,565,602

[45] Date of Patent: Oct. 15, 1996

[54] PRODUCTION OF THIOLCARBAMATES

[75] Inventors: Michael S. Matson; Dean E. Stinn; Michael D. Mitchell, all of Bartlesville, Okla.

[73] Assignee: Phillips Petroleum Company, Bartlesville, Okla.

[21] Appl. No.: 403,042

[22] Filed: Mar. 13, 1995

[51] Int. Cl.$^6$ ............ C07C 333/04; C07C 333/08; C07C 333/12

[52] U.S. Cl. ............ 558/242; 558/232; 558/233; 558/239; 558/241

[58] Field of Search ................. 558/232, 233, 558/239, 241, 242

[56] References Cited

U.S. PATENT DOCUMENTS

| | | | |
|---|---|---|---|
| 3,151,119 | 9/1964 | Grisley et al. | 260/293.4 |
| 3,167,571 | 1/1965 | D'Amico et al. | 260/455 |
| 3,235,333 | 2/1966 | Swakon et al. | 23/203 |
| 3,282,978 | 11/1966 | Swakon | 260/455 |
| 3,392,197 | 7/1968 | Swakon | 260/553 |
| 3,629,311 | 12/1971 | Anderson et al. | 260/455 B |
| 3,954,729 | 5/1976 | Sato et al. | 260/239 B |
| 4,071,423 | 1/1978 | Pitt | 204/158 R |
| 4,248,779 | 2/1981 | Sato et al. | 260/239 BF |
| 4,613,461 | 9/1986 | Viski et al. | 540/608 |

*Primary Examiner*—Johann Richter
*Assistant Examiner*—Laura L. Stockton
*Attorney, Agent, or Firm*—Lucas K. Shay

[57] ABSTRACT

A process which can be used for producing thiolcarbamates is provided wherein the process comprises contacting a reaction mixture with a hydrocarbyl chloride such as, for example, benzyl chloride under a condition which is sufficient to produce a product mixture wherein the reaction mixture comprises carbonyl sulfide, an amine such as, for example, a secondary amine, a solvent; the solvent comprises a tertiary amine; and the reaction mixture, hydrocarbyl halide, and solvent are each present in an amount sufficient to effect the production of a thiolcarbamate. Optionally, the reaction mixture can also comprise a metal hydroxide. Further optionally, the product mixture can be contacted with a metal hydroxide if the reaction mixture does not comprise a metal hydroxide.

37 Claims, No Drawings

PRODUCTION OF THIOLCARBAMATES

FIELD OF THE INVENTION

The present invention relates to a process for producing thiolcarbamates.

BACKGROUND OF THE INVENTION

Thiolcarbamates are an important class of industrial chemicals which can be used as intermediates for synthesis of other chemicals. Many thiolcarbamates have also been used as herbicides, insecticides, and fungicides or bacteriocides for inhibiting the growth of microorganisms.

A thiolcarbamate such as, for example, S-ethyldipropylthiolcarbamate, has been prepared by reacting a secondary amine such as dipropylamine with phosgene to produce a carbamoyl chloride. The carbamoyl chloride is in turn reacted with a thiolate such as sodium alkylmercaptide to produce the corresponding thiolcarbamate. However, using phosgene is generally a safety concern because of its toxicity. Additionally, when phosgene is used, two, three if the alkyl mercaptide is made from an alkylhalide, mole equivalents of halide waste are produced as by-products.

A thiolcarbamate has also been prepared by reacting two mole equivalents of a secondary amine with carbonyl sulfide, in the presence of an aromatic solvent such as, for example, toluene to form a thiolcarbamic acid which further reacts with a hydrocarbyl chloride such as, for example, benzyl chloride to produce a thiolcarbamate. Carbonyl sulfide is generally much easier to handle and safer to use than phosgene. Additionally, when carbonyl sulfide is used, only one mole equivalent of halide, or 33–50% that produced using phosgene, is produced thereby having less disposal problem. In this process, however, the hydrocarbyl chloride is added to a reaction medium after formation of a thiolcarbamate salt. The solvent and excess secondary amine are recovered after neutralization with an aqueous caustic solution. The weight percent as well as the productivity of the thiolcarbamate in the crude organic phase using this process is generally very low, for example, about 25 weight %.

Therefore, there is an ever-increasing need for an improved process for producing thiolcarbamates. It would also be a significant contribution to the art if a process having an increased product yield, a simplified process, an improved reaction rate, a shortened reaction time, an increased product productivity, or combinations of two or more thereof can be developed. Because of the large market of thiolcarbamates, seemingly small improvements in the process for producing thiolcarbamates often translate into low manufacturing costs and large savings to consumers.

SUMMARY OF THE INVENTION

An object of the present invention is to provide a process for producing thiolcarbamates at an increased reaction rate, shorter reaction time, higher volume productivity, improved product yield, or combinations of any two or more thereof, as compared to the referenced process(es). Another object of the present invention is to provide a simplified process for producing thiolcarbamates wherein the process does not require the use of a thiol (mercaptan). A further object of the present invention is to provide a process for producing thiolcarbamates wherein the process can be carried out as a one-pot reaction. Still another object of the present invention is to provide a process which does not require the use of two mole equivalents of a secondary amine for producing thiolcarbamates thereby lowering the manufacturing costs of the thiolcarbamates. Yet still a further object of the present invention is to provide a process for producing thiolcarbamates wherein the process employs a substantially one-liquid medium in carrying out the process. Other objects, aspects, and advantages will become apparent as the invention is more fully disclosed hereinbelow.

According to the present invention, a process which can be used for the production of thiolcarbamates is provided. The process comprises contacting carbonyl sulfide, an amine, and optionally, a metal hydroxide with a hydrocarbyl halide wherein the process is carried out in a solvent which comprises a tertiary amine and under a suitable condition to effect the preparation of a thiolcarbamate; and each reactant is present in an amount sufficient to effect the preparation of a thiolcarbamate.

DETAILED DESCRIPTION OF THE INVENTION

The present invention provides a process which comprises contacting a mixture which comprises, or consists essentially of, carbonyl sulfide, an amine, and optionally, a metal hydroxide with a hydrocarbyl halide. The process is carried out in a solvent which comprises a tertiary amine and under a suitable condition which is sufficient to effect the preparation of a thiolcarbamate. The carbonyl sulfide, secondary amine, metal hydroxide, and hydrocarbyl halide are each present in the process medium in an amount sufficient to effect the production of a thiolcarbamate.

According to the present invention, any thiolcarbamate having a general formula of R—C(R1)(R1)—S—C(O)—N(R2)(R3) can be produced by the present invention process where R, each R1, R2, and R3 can be the same or different and are each independently selected from the group consisting of hydrogen, alkyl radicals, alkenyl radicals, alkynyl radicals, cycloalkyl radicals, alkoxy radicals, aryl radicals, alkaryl radicals, aralkyl radicals, and combinations of any two or more thereof. However, if R2 is hydrogen, R3 is preferably not a hydrogen, and vice versa. Each radical can also be substituted with any radical or combinations of any two or more of the radicals disclosed immediately above. Additionally, if the radicals contain a phenyl group, the phenyl group can also be substituted with halo group, cyano group, or combinations thereof. Generally, R, R1, R2, or R3 can each contain up to about 30, preferably 20, and most preferably 15 carbon atoms. The presently preferred R is a phenyl group. The presently preferred R1 is hydrogen. Presently, it is preferred that R2 and R3 are not hydrogen. The presently preferred R2 is ethyl radical. The presently preferred R3 is 1,2-dimethylpropyl radical.

Examples of thiolcarbamates that can be produced by the invention process include, but are not limited to, S-ethyl dipropylthiolcarbamate, S-2-chloroallyl diethylthiolcarbamate, S-propyl dipropylthiolcarbamate, S-propyl ethylbutylthiolcarbamate, S-allyl diisoproylthiolcarbamate, S-allyl di-n-propylthiolcarbamate, S-ethyl diisobutylthiolcarbamate, S-ethyl ethylcyclohexylthiolcarbamate, S-benzyl ethyl-1,2-dimethylpropylthiolcarbamate, S-benzyl dipropylthiolcarbamate, S-p-chlorotolyl diethylthiolcarbamate, S-ethyl diethylthiolcarbamate, S-ethyl hexamethylene thiolcarbamate, S-benzyl dimethylthiolcarbamate, S-p-chlorobenzyl diethylthiolcarbamate, S-p-ethylbenzyl dibenzylthiolcarbamate, S-p-iso-propylbenzyl-N-ethyl-N-phenylthiolcarbamate, S-p-methoxybenzyl dimethylthiolcarbamate, S-p-ethoxybenzyl hexamethylenethiolcarbamate, S-p- methylthiobenzyl tetramethylenethiolcarbamate, S-p-ethylthiobenzyl diallylthiolcarbamate, S-p-nitrobenzyl bis(2-hydroxyethyl)thiolcarbamate, S-2,6-dichlorobenzyl dimethylthiolcarbamate, S-p-chloro-o-methoxybenzylbutylmethylthiocarbamate, S-2-chloro-4-nitrobenzyl pentamethylenethiolcarbamate, S-2-5-dimethylbenzyl dimethylthiolcarbamate, S-3,5-dinitrobenzyl diethylthiolcarbamate, and combinations of any two or more thereof. The presently preferred thiolcarbamates are S-benzyl ethyl-1,2-dimethylpropylthiolcarbamate and S-benzyl dipropylthiolcarbamate because of their wide use as herbicides.

Carbonyl sulfide can be either purchased commercially or produced by any methods known to one skilled in the art. For example, carbonyl sulfide can be prepared from elemental sulfur and carbon monoxide by the processes disclosed in U.S. Pat. No. 3,235,333, disclosure of which is herein incorporated by reference.

According to the present invention, any amine having the formula of HN(R2)(R3), where R2 and R3 are the same as those disclosed above, can be used for producing thiolcarbamates. Examples of suitable amines include, but are not limited to, methylamine, ethylamine, n-propylamine, isopropylamine, n-butylamine, isobutylamine, tert-butylamine, n-amylamine, isoamylamine, sec-amylamine, tert-amylamine, 1,2-dimethyl-propylamine, n-hexylamine, cyclohexylamine, aniline, allylamine, methallylamine, benzylamine, N-ethyl-1,2-dimethylpropylamine, N-isobutylallylamine, N-allylmethallylamine, N-allylmethallylamine, N-propylmethallylamine, N-ethylmethallylamine, N-propargylpropylamine, bis-(2-chloroallyl)amine, trimethylene diamine, ethylene diamine, 2-methoxy-ethylamine, 3-methoxypropylamine, aniline, p-anisidine, p-phenetidine, p-toluidine, 3,4-dichloroaniline, and 2-cyanoethylamine, dimethylamine, diethylamine, dipropylamine, diisopropylamine, dibutylamine, diamylamine, diisobutylamine, diallylamine, bis(2-methoxyethyl)amine, bis(2-phenoxyethyl)amine, bis(2-benzyloxyethyl)amine, piperidine, 5-ethyl-2-methylpiperidine, morpholine, 2,6-dimethylmorpholine, piperazine, 2,5-dimethylpiperazine, pyrrolidine, 4-phenylpiperazine, 2-methylpiperidine, 5-ethyl-3-methylpiperidine, N-(2-chloroallyl)isopropylamine, N-(2-chloroallyl)propylamine, N-ethylaniline, N-allylisopropylamine, N-allylpropylamine, N-allylbutylamine, N-(2-cyanoethyl)isopropylamine, N-(2-chloroallyl)-3-methoxypropylamine, N-ethylcyclohexylamine, N-methylcyclohexylamine, N-ethyl-isoamylamine, N-methylbutylamine, N-ethylbutylamine, N-(2-chloroallyl)allylamine, N-(3-chloroallyl)allylamine, N-(3-chloroallyl)ethylamine, N-(3-chloroallyl)propylamine, and combinations of any two or more thereof. The presently preferred amine is a secondary amine. The presently preferred secondary amines are N-ethyl-1,2-dimethylpropylamine and dipropylamine because the thiolcarbamates produced therefrom have been widely used as herbicides.

Any metal hydroxide that can form a metal salt of a thiolcarbamate can be used in the present invention. Preferably the metal hydroxide is an alkali metal hydroxide, an alkaline earth metal hydroxide, or combinations of any two or more thereof. Examples of the preferred metal hydroxides include, but are not limited to, lithium hydroxide, sodium hydroxide, potassium hydroxide, calcium hydroxide, magnesium hydroxide, and combinations of any two or more thereof. The presently most preferred metal hydroxide is sodium hydroxide because it is readily available and is inexpensive. The metal hydroxide can be in either solid form or aqueous solution, preferably in aqueous solution.

According to the present invention, any hydrocarbyl halide having the formula of R—C(R1)(R1)—X, wherein each R1 can be the same or different and R and R1 are the same as those disclosed above and X is a halide, can be used. Examples of suitable hydrocarbyl halide include, but are not limited to, benzyl chloride, benzyl bromide, benzyl iodide, ally chloride, allyl bromide, allyl iodide, 2-chloroallyl chloride, 2-chloroallyl bromide, methallyl chloride, methallyl bromide, fluorobenzyl chlorides, fluorobenzyl bromides, chlorobenzyl chlorides, chlorobenzyl bromides, bromobenzyl chlorides, bromobenzyl bromides, iodobenzyl chlorides, methylbenzyl chlorides, methylbenzyl bromides, nitrobenzyl chlorides, nitrobenzyl bromides, cyanobenzyl chlorides, cyanobenzyl bromides, 4-ethylbenzyl chloride, 4-(isopropyl)benzyl chloride, 4-(isopropyl)benzyl chloride, 2-methoxybenzyl chloride, 3-ethoxybenzyl bromide, 4-(isopropoxy) benzyl chloride, 4-methylthiobenzyl chloride, 4-ethylthiobenzyl chloride, dichlorobenzyl chlorides, 4-chloro-2-methoxybenzyl chloride, 2-chloro-4-nitrobenzyl chloride, 2,5-dimethylbenzyl chloride, 4-methyl-3-nitrobenzyl chloride, 3,5-dinitrobenzyl chloride, and combinations of any two or more thereof. The presently preferred hydrocarbyl halide is benzyl chloride.

The solvent suitable for the present invention is a tertiary amine having the formula of $N(R4)_3$ wherein each R4 can be the same or different and is each independently selected from the group consisting of alkyl radicals, alkoxy radicals, alkenyl radicals, alkynyl radicals, aryl radicals, alkaryl radicals, cycloalkyl radicals, cycloalkenyl radicals, and combinations of any two or more thereof. Each radical disclosed herein can contain from 1 to about 30, preferably 1 to about 20, and most preferably 1 to 15 carbon atoms. The presently preferred R4 is each an ethyl radical.

Examples of suitable solvents include, but are not limited to, trimethylamine, triethylamine, tri-n-propylamine, tri-n-butylamine, triisopropylamine, methyl-diethylamine, methyl-di-n-propylamine, methyl-diisopropylamine, ethyl-dimethylamine, ethyl-di-n-propylamine, ethyl-diisopropylamine, tri-t-butylamine, amyl-diisoamylamine, and combinations of any two or more thereof. The presently preferred solvent is triethylamine because it is readily available and easy to handle.

According to the present invention, the molar ratio of secondary amine to carbonyl sulfide can be any effective ratio that can produce a thiolcarbamate. Generally, the ratio can range from about 0.5:1 to about 2:1, preferably about 0.75:1 to about 1.25:1, and more preferably about 0.9:1 to about 1.1:1, and most preferably about 1:1.

The molar ratio of metal hydroxide, if present in the reaction medium, to carbonyl sulfide can be any effective ratio which can substantially recover the tertiary amine solvent used or substantially neutralize the tertiary amine-hydrogen halide produced in the invention process. Generally, the ratio can be in the range of from about 0.1:1 to about 3:1, preferably about 0.5:1 to about 1.5:1, and more preferably about 0.9:1 to about 1.1:1, and most preferably about 1:1. Presently it is preferred that the metal hydroxide is added to the process medium after a thiolcarbamate is produced.

The molar ratio of hydrocarbyl halide to carbonyl sulfide can also be any effective ratio which can produce a thiolcarbamate. Generally, the ratio can be in the range of from about 0.5:1 to about 2:1, preferably about 0.75:1 to about 1.25:1, and more preferably about 0.9:1 to about 1.1:1, and most preferably about 1:1.

The molar ratio of solvent to carbonyl sulfide can also be any effective ratio that can facilitate the production of a thiolcarbamate and can be in the range of from about 1:1 to about 100:1, preferably about 1:1 to about 50:1, more preferably about 1.5:1 to about 20:1, and most preferably 1.5:1 to 3:1.

According to the present invention, the process can be carried out under a condition sufficient to effect the preparation of a thiolcarbamate. The condition can include a temperature in the range of from about −10° C. to about 80° C., preferably about −10° C. to about 60° C., more preferably about 0° C. to about 50° C., and most preferably 2° C. to 40° C.; a pressure in the range of from about 0.5 to about 10, preferably about 1 to about 5, more preferably about 1 to about 3, and most preferably about 1 to 2 atmospheres; and a total reaction time of from about 1 to about 30, preferably about 2 to about 20, and most preferably 3 to 15 hours.

According to the present invention, carbonyl sulfide can also be produced in-situ in which elemental sulfur and carbon monoxide are combined in a reaction vessel containing a solvent with an amine to produce carbonyl sulfide and thereafter, the carbonyl sulfide is further contacted with the amine and hydrocarbyl halide, optionally a metal hydroxide, and a solvent under a suitable condition, as disclosed above, for the production of a thiolcarbamate. According to the present invention, the term "in-situ" refers to, unless otherwise indicated, the production of carbonyl sulfide in a reaction vessel for use as a reagent for the production of thiolcarbamates as compared to the use of a purchased carbonyl sulfide. Again, as disclosed above, the presently preferred process is to add a metal hydroxide to a thiolcarbamate that has been produced.

In the process where the carbonyl sulfide is produced in-situ, the mole ratio of carbon monoxide to sulfur generally can be any effective ratio for the production of carbonyl sulfide and can be in the range of from about 5:1 to about 1:1, preferably about 3:1 to about 1:1, and most preferably 2:1 to 1:1 for most efficient production of carbonyl sulfide. The molar ratios of secondary amine to carbonyl sulfide, hydrocarbyl halide to carbonyl sulfide, metal hydroxide to carbonyl sulfide, and solvent to carbonyl sulfide can be the same as disclosed above. The condition for carrying out the process in which the carbonyl sulfide is produced in-situ can be the same as that disclosed above with the exception that in the step for production carbonyl sulfide, the temperature is generally in the range of from about 50° to about 300° C., preferably abut 70° to about 200° C., and most preferably 90° to 130° C. for about 1 to about 20 hours; and the pressure is generally in the range of from about 0.5 to about 50, preferably and preferably about 10 to about 30 atmospheres.

After a desired thiolcarbamate is produced, the thiolcarbamate can be further processed, including separation, purification, recovery, modification, or combinations of any two or more thereof. These processing steps can be carried out according to any method known to one skilled in the art such as, for example, phase separation, distillation, vacuum stripping, chromatography, crystallization, complexation, and combinations of any two or more thereof. Because these methods are well known to one skilled in the art, a detailed description thereof is omitted herein for the interest of brevity.

The following examples are provided to further illustrate the present invention and are not intended to be construed to unduly limit the scope of the present invention.

In the following tables, some temperature profiles are reported in two temperatures separated by semicolons (;). The first number was the starting temperature and the second number was the finishing temperature.

EXAMPLE I

This example illustrates the process of the invention wherein carbonyl sulfide was produced in-situ.

The "in-situ" reactions to prepare COS were done in either a 300 cc or 1.0 liter autoclave. The clean reactor was purged with nitrogen. Elemental sulfur and N-ethyl-1,2-dimethylpropylamine (EDMPA) were added in the desired quantities. Any solvent being used was also added. The reactor was then sealed and purged with nitrogen. CO was then introduced into the reactor at the desired pressure and the reaction mixture heated to the desired temperature, usually 70°–90° C. The CO usage was monitored in the same way hydrogen consumption is tracked for hydrogenation reactions. When CO uptake was negligible, <1 psig pressure drop in 5 minutes, the reaction was considered complete. The reaction mix was then cooled and transferred to another vessel containing the aqueous caustic solution. After neutralization, the benzyl chloride (BzCl) was then added slowly.

In several runs (6, 7, 37 in Table I) the neutralization and benzyl chloride additions were done in the same reactor by addition of these reagents to the reactor. The caustic or BzCl were charged to another vessel which was connected to the reactor. The small vessel was pressured and the contents transferred to the other reactor by opening the appropriate valves. After the BzCl addition was complete, there was generally an additional reaction time, frequently at a higher temperature. When the reaction had proceeded for the desired time, the reaction was halted by cooling, if necessary, and dumping the reaction mixture. When aqueous caustic is present in the system, there are two liquid phases. The top organic phase contains the thiolcarbamate (TCB) product, solvent and any organic base present, such as EDMPA or triethylamine (TEA). The top phase was separated and in some cases the TCB was recovered by removing the lights by using the rotoevaporator. Samples were removed from the reactor periodically for GC analysis. The TCB was recovered by vacuum distillation of the solvent and unreacted reagents and the TCB obtained as a kettle product.

The GC analysis was done using a HP 5890 Gas Chromatograph and a HP 3365 Chem Station data acquisition system, a 30 meter HP-5 (methyl-5%-phenyl-silicone) capillary column, 0.32 mm diameter and 0.25 micron film thickness. An FID detector was used. The GC parameters are as follows:

| | |
|---|---|
| Inlet temperature | 250° C. |
| Detector temperature | 300° C. |
| Inlet pressure | 5.4 psi (@ 50° C.) |
| Carrier gas | helium |
| Oven Profile: | |
| Initial temperature | 50° C. |
| Initial time | 5.0 minutes |
| Ramp rate | 10° C./min. |
| Final temperature | 240° C. |
| Final time | 11.0 minutes |

Table I lists the results of runs in which COS was prepared by reaction of sulfur and CO. These runs clearly demonstrate that COS can be prepared and reacted with benzyl chloride to form the TCB. In several runs, only one equivalent of EDMPA was used. The second equivalent of amine was added as either TEA or pyridine.

Tetrahydrofuran (THF) was used as solvent in runs 1, 2, 5 and 6. In runs 2 and 6 the EDMPA/S mole ratio was 2:1.

The time required for COS production was about 2 hours. This was determined by monitoring the CO up-take and the reaction was considered done when this appeared to stop. Only moderate yields and purity of TCB were obtained. In runs 1 and 5, the EDMPA/S ratio was only 1:1. However, in run 1, TEA was added to serve as the amine base. Too much benzyl chloride was used in this run which resulted in low recovered yield and purity. In run 5, only one equivalent of EDMPA was used and resulted in an even lower conversion of the benzyl chloride. The yields of TCB were based on the amount of sulfur charged to the reactor initially.

Run 3 used heptane as solvent. Again the benzyl chloride was not completely reacted, but it was evident TCB can be prepared this way, but the reaction time to prepare the COS "in-situ" was substantially longer (8 hours vs. 2 hours) and a higher reaction temperature was required. When no solvent was used in run 4, the reaction time to produce COS was long and the final yield to TCB low.

In run 7, toluene was used as solvent and the mole ratio of EDMPA/S was 2:1. The reaction time to produce COS was intermediate to that seen with THF and heptane. Although the benzyl chloride conversion appeared high, the recovered yield was only 89% for the TCB with a purity of only 81%. When the amount of EDMPA was cut in half(run 10), the reaction time to produce COS was long and the temperature was higher (90° C. vs. 70° C.). Not only was there incomplete utilization of the benzyl chloride, there was a significant production of benzyl mercaptan, an unwanted by-product. Benzyl mercaptan production not only lowers the TCB yield but introduces a hard to remove impurity into the TCB crude.

Runs 8 and 9 used toluene as solvent and pyridine as the amine base. The production of COS appeared to be normal, but substantial quantities of water had to be added to the reactor to produce a workable solution for addition of the benzyl chloride.

Run 31 was an attempt to prepare the TCB by using TEA as the solvent and amine base and by also having the benzyl chloride present during the entire reaction sequence. Very low utilization of EDMPA was observed and therefore low TCB production. Conversion of benzyl chloride was high with the production of at least three new by-products.

Run 37 again used TEA as solvent and amine base. However, COS production was done at 90° C. in 4 hours. The reaction crude was cooled and the benzyl chloride added. It was necessary to add some water to obtain a more workable solution and to obtain a sample from the reactor. The final recovered yield was 84 weight % with a TCB purity of 97.8%.

The results presented in Table I demonstrate that TCB can be prepared by first producing the COS followed by reaction of this crude intermediate with caustic and benzyl chloride. If excess secondary amine was used or another amine such as pyridine or TEA was present, caustic may not be required.

TABLE I

Thiolcarbamates via "in-situ" COS Production

|  | Run 1 | Run 2 | Run 3 | Run 4 | Run 5 | Run 6 | Run 7 |
|---|---|---|---|---|---|---|---|
| COS Formation | | | | | | | |
| Reactor | R3 | R3 | R3 | R3 | R3 | R5 | R5 |
| Solvent | THF | THF | Heptane |  | THF | THF | Toluene |
| amount | 71.0 g | 71.0 g | 80 cc |  | 40 cc | 200 g | 225 cc |
| Wt. EDMPA (g) | 46.5 | 95.0 | 95.0 | 95.0 | 47.5 | 231.0 | 231.0 |
| Wt. Sulfur (g) | 12.8 | 12.8 | 12.8 | 12.8 | 6.4 | 32.0 | 32.0 |
| Other reagents (g) | TEA (40.9) | | | | | | |
| CO Pressure (psig) | 400 | 200 | 400 | 400 | 400 | 200 | 200 |
| Reaction Temp (°C.) | 70 | 70 | 90 | 70 | 70 | 70 | 70 |
| Reaction Time (hrs) | 2.00 | 2.36 | 8.00 | 8.46 | 1.80 | 2.12 | 4.70 |
| Neutralization | | | | | | | |
| Reactor | glass | glass | glass | R2 | R2 | R5 | R5 |
| Wt. NaOH (g) | 16.0 | 16.0 | 16.0 | 16.0 | 8.0 | 40.0 | 40.0 |
| Wt. Water (g) | 50.0 | 200.0 | 200.0 | 50.0 | 20.0 | 80.0 | 80.0 |
| Time (hrs) | 0.60 | 0.50 | 0.75 | 0.33 | 0.25 | 0.67 | 0.10 |
| Temp. (°C.) | 5.0 | 5.0 | 5.0 | −10.0 | 19 ; 23 | 15 ; 25 | 20.0 |
| Alkylation | | | | | | | |
| Reactor | glass | glass | glass | glass | glass | R5 | R5 |
| Wt. BzCl (g) | 57.0 | 57.0 | 57.0 | 57.0 | 25.5 | 127.0 | 127.0 |
| Addition Time (hrs) | 0.75 | 1.50 | 0.25 | 0.12 | 0.12 | 0.67 | 1.50 |
| Addition Temp. (°C.) | 0 ; 5 | 0 ; 25 | 5 | 7 | 25 ; 35 | 25 ; 30 | 30 |
| Additional Solvent | | | | | | | |
| Reaction Time (hrs) | 2.00 | 1.00 | 3.00 | 5.10 | 2.00 | 1.50 | 2.00 |
| Reaction Temp. (°C.) | 25 | 50 | 50 | 35 ; 50 | 35 ; 57 | 30 | 30 |
| Mole Ratio | | | | | | | |
| EDMPA/S | 1.00 | 2.07 | 2.07 | 2.07 | 1.03 | 2.01 | 2.01 |
| BzCl/Sulfur | 1.11 | 1.11 | 1.11 | 1.11 | 1.00 | 1.00 | 1.00 |
| % TCB in crude | 29.69 | 41.42 | 34.05 | 53.49 | 33.98 | 44.11 | 31.22 |
| % EDMPA in crude | 8.58 | 28.17 | 24.98 | 36.80 | 31.33 | 24.69 | 16.83 |
| % BzCl in crude | 11.04 | 2.36 | 3.34 | 6.66 | 7.15 | 1.25 | 0.11 |
| % Solvent in crude* | 49.82 | 26.41 | 33.83 |  | 25.70 | 28.15 | 50.25 |
| Ratio BzCl/TCB | 0.37 | 0.06 | 0.10 | 0.12 | 0.21 | 0.03 | <0.01 |
| Ratio BzSH/TCB | nd | 0.02 | 0.08 | 0.01 | 0.02 | 0.01 | nd |

TABLE I-continued

| Thiolcarbamates via "in-situ" COS Production | | | | | | | |
|---|---|---|---|---|---|---|---|
| Patio DTCB/TCB | nd | nd | nd | nd | nd | nd | 0.05 |
| Recovered weight | 80.5 | 97.2 | 87.5 | | | 244.8 | 241.9 |
| % Purity TCB | 74.6 | 90.7 | 83.4 | 84.5 | 79.2 | 93.2 | 88.9 |
| Recovered Yield | <57 | 83 | 70 | | | 86.1 | 81.2 |

| | Run 8 | Run 9 | Run 10 | Run 11 | Run 12 | Run 31 | Run 37 |
|---|---|---|---|---|---|---|---|
| COS Formation | | | | | | | |
| Reactor | R5 | R5 | R5 | R5 | R5 | R5 | R5 |
| Solvent | Toluene | Toluene | Toluene | Toluene | Toluene | TEA | TEA |
| amount | 225 cc | 225 cc | 300 cc | 200 c | 200 cc | 303 g | 303 g |
| Wt. EDMPA | 115.0 | 115.0 | 115.0 | 230 {3} | 230.0 | 121.0 | 120.0 |
| Wt. Sulfur | 32.0 | 32.0 | 32.0 | 32.0 | 32.0 | 33.0 | 34.0 |
| Other reagents (g) | Pyridine (80) | Pyridine (80) | | Na-pentoxide (1) | Na-pentoxide (0.5) | BzCl (127) | |
| CO Pressure (psig) | 200 | 200 | 300 | 230 | 400 | 300 | 350 |
| Reaction Temp (°C.) | 70 | 70 | 90 | 32 | 20 ; 90 | 100 | 90 |
| Reaction Time (hrs) | 2.21 | 2.00 | 8.25 | 5.00 | 3.00 No Rxn (leak in CO after fixed no reaction) | 8.00 | 4.00 |
| Neutralization | | | | | | | |
| Reactor | {1} | R5 | R5 | | | | |
| Wt. NaOH (g) | | 40.0 | 40.0 | | | | |
| Wt. Water (g) | | 80.0 | 160.0 | | | | |
| Time (hrs) | | 0.10 | 1.50 | | | | |
| Temp. (°C.) | | 20.0 | 25.0 | | | | |
| Alkylation | | | | | | | |
| Reactor | R5 | glass | glass | R5 | | | R5 |
| Wt. BzCl | 127.0 | 127.0 | 127.0 | 127.0 | | | 127.0 |
| Addition Time (hrs) | 0.25 | 2.50 | 3.00 | 0.10 | | | 1.00 |
| Addition Temp. (°C.) | 20 | 25 | 25 | 25 | | | 25 |
| Additional Solvent | 850 cc (H2O) | 200 cc (H2O) | {2} | | | | 200 cc (H2O) |
| Reaction Time (hrs) | 5.00 | 3.00 | | 2.00 | | | 2.00 |
| Reaction Temp. (°C.) | 25 | 25 ; 50 | | 50 | | | 25 |
| Mole Ratio | | | | | | | |
| EDMPA/S | 1.00 | 1.00 | 1.00 | 2.00 | 2.00 | 1.02 | 0.98 |
| BzCl/Sulfur | 1.00 | 1.00 | 1.00 | 1.00 | | 0.97 | 0.94 |
| % TCB in crude | 16.44 | 24.07 | 9.81 | 0.07 | nd | 6.45 | 52.82 |
| % EDMPA in crude | 3.26 | 1.70 | 2.04 | 27.17 | 48.64 | 17.96 | 1.663 |
| % BzCl in crude | 3.07 | 2.33 | 9.40 | 11.46 {4} | nd | nd {5} | 0.75 |
| % Solvent in crude* | 76.38 | 67.61 | 69.78 | 60.07 | 51.03 | 29.98 | 43.94 |
| Ratio BzCl/TCB | 0.19 | 0.10 | 0.96 | | | | 0.01 |
| Ratio BzSH/TCB | nd | 0.15 | 0.79 | | | | nd |
| Ratio DTCB/TCB | 0.016 | 0.024 | 0.069 | | | | <0.001 |
| Recovered weight | | | | No Rxn. | | | 228.2 |
| % Purity TCB | | | | | | | 97.8 |
| Recovered Yield | | | | | | <10 | 84.2 |

R5 = 1 liter Autoclave (316SS); R2 = 300 cc Autoclave (316SS); R3 = 300 cc Autoclave (Hasteloy C).
BzCl = Benzyl chloride; EDMPA = N-ethyl-1,1-dimethyl propylamine.
TCB = Thiolcarbamate (R2R3N-CO-S-R3; R1 = ethyl; R2 = 1,2-dimethylpropyl; R = benzyl).
DTCB = Dithiocarbamate (R2R3N-CS-S-R).
nd = Not detected.
*Did not include water.
{1} Added 850 cc water to clear solids from reactor, stirred for additional 4 hrs at 50° C.
{2} Additional 200 cc water added to R5 to remove crude before alkylation step.
{3} Added after CO reaction appeared to be done.
{4} 1.15% benzyl mercaptan.
{5} Very little thiolcarbamate, 3 new products based on BzCl.

EXAMPLE II

This example illustrates the invention process for producing a thiolcarbamate using carbonyl sulfide.

Most of the runs using carbonyl sulfide purchased from Matheson Chemicals (Secaucus, N.J.) were conducted in either a 500 cc or 1000 cc baffled glass reactor. An air-driven mechanical stirrer was used for mixing the solution. The reactor contained a thermowell and a dispersion tube through which the COS was added to the solution. The reactor was maintained under a slight positive pressure of nitrogen. The COS was contained in a small pressure cylinder which was set on a balance. The COS sent to the reactor was monitored both by weight loss and by use of a rotometer. The desired reaction temperature was maintained by use of water or ice bath. To perform a typical reaction, the solvent and EDMPA were added to the dry, clean and purged reactor. In some cases aqueous caustic, water or BzCl were also added to the reactor initially, depending on the reaction conditions being investigated. The COS was then added through the dispersion tube, generally over a 1–4 hour time period. The reaction temperature was maintained at the desired level by the use of the water or ice bath. The reaction is moderately exothermic. After the COS addition was complete, then either BzCl, caustic or other solvent might be added depending on whether they were present initially and the conditions being checked. Frequently, additional reaction time was required and occasionally the temperature was raised to 30°–40° C. range by use of a heating mantle. Samples were removed from the reactor periodically for GC analysis as described above. The TCB was recovered by vacuum distillation of the solvent and unreacted reagents and the TCB obtained as a kettle product, as described above.

Table II lists the results of a series of runs where COS that was purchased from Matheson was used. Several options were investigated. Several solvents were investigated. The addition of COS was done in some cases to the solvent with the EDMPA only followed by benzyl chloride addition either before or after neutralization with caustic. In some cases the caustic or other base was present initially along with the EDMPA.

In this example, benzyl chloride was used as the limiting reagent.

Four runs were made using toluene as solvent. Reasonable results (run 15) were obtained when COS was added to the toluene containing two equivalents of EDMPA followed by neutralization with caustic and then benzyl chloride addition. Similar results (run 16) were obtained when COS was added to the reactor containing toluene, EDMPA and caustic followed by addition of benzyl chloride. However, if COS was added to the system (run 14) which contained caustic but only one equivalent of EDMPA, then benzyl chloride utilization was very poor. In run 13, the caustic was added at the end of the reaction. The results were intermediate to the others. This may have been the result of halting the reaction too soon. The reaction time in this run was only 5.5 hours vs. 8–9 hours for the other runs.

Run 17 used no solvent but had the aqueous caustic solution present during the COS addition. The benzyl chloride was then added to produce after 9.5 hours a recovered TCB yield of 84 weight % with a purity of 98.1%.

Run 18 started out using EDMPA only as the solvent with no added caustic. COS was added over a 3 hour period followed by the benzyl chloride addition. After the addition, ether was added as a diluent because the reaction mixture was becoming very viscous. Incomplete conversion of the benzyl chloride was observed. This method would require very good recovery of the excess EDMPA because of the high expense of EDMPA.

For comparison purposes, run 22 used THF as solvent and ammonium hydroxide was used as the base and was present at the start of the COS addition which required 3.25 hours. Benzyl chloride was added and the reaction allowed to proceed for 8.25 hours. The crude product contained 42.7% TCB and 1.83% unreacted BzCl. The crude also contained 3.9% benzyl mercaptan and 5.4% benzyl sulfide.

A series of runs were made using TEA as the solvent and also as the amine base. A ratio of about 2–3 moles of TEA were used per mole of benzyl chloride. EDMPA was used in a slight excess and BzCl was the limiting reagent as a slight excess of COS was added to the reactions.

In addition, some runs were made where the BzCl was present initially as the COS was added. Also, there were runs made where water, ether or pentane were added at various points in the reaction to determine the influence of solvent.

In run 19, TEA was used in a 2:1 mole ratio vs. EDMPA. COS addition required 3.5 hours and BzCl addition required 2.4 hours, after which 100 g of water was added. Reaction was carried out for an additional 2 hours. The reactor yield of TCB, based on total weight charged to the reactor was 43%; if water was excluded from calculation, the yield was 52%. The recovered TCB yield was 85 weight % with a purity of 97.5%. The crude (organic liquid phase) contained 70.3% TCB and only 0.04% unreacted BzCl. No caustic was added to the crude to release the TEA tied up as the hydrochloride salt for the calculation of TCB.

In run 20, caustic was added after the BzCl addition. Additional water was added to dissolve the solids. Although the reaction went fairly well, there was still 5.35% BzCl in the crude along with 50.1% TCB.

In run 21, pentane was used as the solvent with one equivalent of COS added to one equivalent of EDMPA and TEA. The BzCl was added after COS addition was complete. The reaction time was considerably longer (13 hours vs. 8–9 hours) but there was still incomplete reaction of the BzCl.

Run 23 was similar to run 19 except that the COS addition time was shorter and the water was added to the reaction mixture 3 hours after the BzCl addition instead of immediately after the addition. The crude organic phase contained 66.3% TCB, 0.07% unreacted BzCl and resulted in a recovered yield of 86.1 weight % with a purity of 98.4%.

A TEA to BzCl ratio of 3:1 was used in run 24. No water or other solvent was added during this run. The crude was treated with aqueous caustic at the end of 8 hours. The crude contained 40.8% TCB and 0.2% unreacted BzCl. The recovered yield of TCB was 88.7 weight % with a purity of 98.4%.

A 2:1 TEA to BzCl ratio was used in run 26 along with ether as the solvent. After 10 hours of reaction, the crude contained 39.1% TCB and 1.56% unreacted BzCl.

Run 27 is similar to run 24 but with a shorter reaction time (7.3 hours vs. 8.1 hours) and a slightly higher reaction temperature (37° C. vs. 30° C. final temperature). The recovered TCB yield was 89.1% with a purity of 97.7%.

In runs 28 through 36, BzCl was present initially along with the TEA and EDMPA while COS was added to the reactor. The best run (33) used a TEA to BzCl mole ratio of 2:1. The COS was added over a 2 hour period at 25° C. The reaction was allowed to continue for an additional 2 hours at which time one equivalent of caustic (16.7 weight %) was added. The organic crude contained 50.9% TCB and 0.17% BzCl. The TCB recovered yield was 94.4% weight % with a purity of 98.5%. A similar reaction (run 28) resulted in only a 89.3% weight % recovered yield with a purity of 97.7%. In that run, the COS was added at <10° C. but the total reaction time was 7.7 hours vs. 4 hours for the better run. Also, the TEA to BzCl ratio was 3:1 in run 28. Run 29 also used the higher TEA to BzCl ratio but the COS was added at 25° C. and the total reaction time was 6 hours. The TCB recovered yield was 92.2 weight % with a purity of 98.1%. It appeared that short reaction times at a reaction temperature of 25° C. produced good yields of TCB.

Good results were also obtained if water was added to the reaction 1 to 2 hours after the COS addition was complete (runs 32 and 36). Run 36 was run at twice the volume of the other runs but the ratios of reactants were the same. Also, run 36 was a shorter reaction and used two-thirds the amount of water as run 32. The TCB recovered yields were 94.2 and 95.6 weight % for runs 32 and 36 respectively while the TCB purity was essentially 98.2% in both runs. In run 36, when caustic was added after the reaction, 85% of the TEA was recovered from the water phase. When water was added to a reaction (run 34) which also had caustic present initially, then the TCB recovered yield was only 76.7 weight % with a purity of 87.1%. The product also contained 3.5% benzyl mercaptan and 0.7% benzyl sulfide.

Several other runs were made for comparative reasons. In one run, tributylamine was used in place of TEA (run 35). This reaction did not proceed as well, even at 41° C. After 9 hours, the crude contained 21.2% of thiolcarbamate and 6.75% unreacted BzCl. Another run (30) used butyl chloride in place of BzCl. This run indicated that butyl chloride is not as reactive under these conditions as is benzyl chloride.

In summary, good yields of high purity TCB were produced when 1.0–1.05 equivalents of COS was added to solution containing 1.0–1.05 equivalents of EDMPA and 1.0 equivalents of BzCl and 2–3 equivalents of TEA as solvent and base. Some water could be added near the end of the reaction to dissolve the solids and helped ensure complete conversion of the BzCl. The reactions were run at 20°–30° C. for 4–5 hours. When treated with aqueous caustic, the TEA was liberated and could be recovered for reuse in good recovered yields (>85%). The TCB was purified by vacuum stripping of the TEA and the slight excess of EDMPA and any unreacted BzCl. The recovered yields were 90–96% with TCB purity of 98–99%.

TABLE II

Thiolcarbamate Production via COS

|  | Run 13 | Run 14 | Run 15 | Run 16 | Run 17 | Run 18 |
|---|---|---|---|---|---|---|
| Reactor | glass | glass | glass | glass | glass | glass |
| Solvent | Toluene | Toluene | Toluene | Toluene |  |  |
| Solvent weight (g) | 300 | 300 | 300 | 300 |  |  |
| Wt. EDMPA (g) | 115 | 57.5 | 115 | 115 | 230 | 250 |
| Wt. COS (g) | 30 | 32 | 32 | 35 | 64 | 63 |
| COS addition Time (hrs) | 1.33 | 2.00 | 1.15 | 1.50 | 2.80 | 3.10 |
| COS addition Temp. (°C.) | 10 | 10 | 10 | 8 | 10 | 12 |
| Wt. BzCl (g) | 64 | 64 | 64 | 64 | 128 | 127.5 |
| When Added | 0.5 hr after COS addn. | After COS | 0.5 hr after base addn. | 0.5 hr after COS addn. | 1 hr after COS addn. | 0.4 hr after COS addn. |
| Time (hrs) | 0.75 | 0.75 | 1.00 | 1.00 | 2.85 | 1.60 |
| Temp. (°C.) | 10 | 10 ; 26 | 4 ; 18 | 8 ; 25 | 8 ; 31 | 12 |
| Additional Rm. Time | 3.00 | 4.50 | 5.00 | 4.75 | 2.80 | 2.50 |
| Additional Rxn Temp. | 25 ; 30 | 26 | 18–34 | 25 | 31 | 22 |
| Additional Solvent |  | Water |  | Water |  | Ether |
| weight (g) |  | 200 |  | 100 |  | 140 |
| When added |  | after 5.5 hrs |  | 2 hrs after BzCl addn. |  | 0.5 hr after BzCl addn. |
| Wt. NaOH (g) | 20 | 20 | 20 | 20 | 40 | 40 |
| Wt. Water (g) | 100 | 100 | 100 | 100 | 300 | 150 |
| When Added | after reaction complete | initially | 0.75 hrs after COS addn. | initially | initially | at end of rxn. |
| Time (hrs) | 0.33 |  | 0.50 |  |  |  |
| Temp. (°C.) | 20 |  | 5 |  |  |  |
| Total Reaction Time (hrs) | 5.50 | 8.25 | 9.00 | 9.00 | 9.50 | 7.33 |
| Temp. Profile | 10 ; 30 | 10 ; 26 | 5 ; 34 | 8 ; 25 | 8 ; 31 | 12 ; 22 |
| Mole Ratio |  |  |  |  |  |  |
| EDMPA/COS | 2.00 | 0.94 | 1.88 | 1.71 | 1.88 | 2.07 |
| BzCl/COS | 1.00 | 0.94 | 0.94 | 0.86 | 0.94 | 0.95 |
| TEA/COS | na | na | na | na | na | na |
| Ratio BzCl/TCB | 0.070 | 0.374 | 0.025 | 0.053 | 0.003 | 0.052 |
| Ratio BzSH/TCB | nd | 0.038 | 0.004 | 0.005 | nd | nd |
| Ratio DTCB/TCB | nd | 0.004 | 0.001 | 0.024 | nd | 0.001 |
| % TCB in Crude Organic | 14.96 | 12.61 | 17.06 | 17.23 | 66.49 | 40.20 |
| % BzCl in Crude Organic | 1.04 | 4.72 | 0.42 | 0.91 | 0.26 | 2.09 |
| % EDMPA in Crude | 16.88 | 0.46 | 8.70 | 7.97 | 32.24 | 36.31 |
| % Solvent in Crude (*) | 67.09 | 81.69 | 73.64 | 73.24 |  | 20.86 |
| Final Recovered Wt. (G) | 109 | 72.1 | 114 | 110 | 226 |  |
| % TCB Purity | 94.7 | 96.6 | 97.6 | 93.9 | 98.1 |  |
| % Recovered Yield | 77.9 | 57.5 | 84.0 | 78.0 | 83.7 |  |

|  | Run 19 | Run 20 | Run 21 | Run 22 | Run 23 | Run 24 |
|---|---|---|---|---|---|---|
| Reactor | glass | glass | glass | glass | R5 | R5 |
| Solvent | TEA | TEA | TEA | THF | TEA | TEA |
| weight (g) | 202 | 202 | 102 | 200 | 202 | 303 |
| Wt. EDMPA (g) | 121 | 121 | 117 | 117 | 121 | 121 |
| Wt. COS (g) | 64 | 64 | 60 | 62 | 64 | 64 |
| COS addition Time (hrs) | 3.50 | 4.20 | 3.75 | 3.25 | 2.25 | 2.20 |
| COS addition Temp. (°C.) | 6 | 7 | 8 | 8 | 2 | 2 |
| Wt. BzCl (g) | 127 | 127 | 127 | 127 | 127 | 127 |
| When Added | 0.5 hr after | 0.5 hr after | 0.5 hr after | after COS | 0.5 hr after | 0.5 hr |

TABLE II-continued

Thiolcarbamate Production via COS

|  | COS addn. | COS addn. | COS addn. | addn. | COS addn. | after COS addn. |
|---|---|---|---|---|---|---|
| Time (hrs) | 2.40 | 2.50 | 2.33 | 2.25 | 0.50 | 0.10 |
| Temp. (°C.) | 7 ; 19 | 7 | 9 | 11 | 4 | 4 |
| Additional Rxn. Time | 4.00 |  |  |  |  | 5.00 |
| Additional Rxn Temp. | 22 |  |  |  |  | 4 ; 30 |
| Additional Solvent | Water | Water | Pentane | NH4OH | Water |  |
| weight (g) | 100 | 100 | 200 | 60 | 100 |  |
| When added | after BzCl addition | 1 hr after NaOH addn. | initially | initially | 3 hrs after BzCl addn. |  |
| Wt. NaOH (g) |  | 40 |  |  |  | 40 |
| Wt. Water (g) |  | 100 |  |  |  | 150 |
| When Added |  | After BzCl addn. |  |  |  | after rxn complete |
| Time (hrs) |  | 0.40 |  |  |  |  |
| Temp. (°C.) |  | 7 |  |  |  |  |
| Total Reaction Time (hrs) | 8.50 | 9.25 | 13.50 | 8.25 | 7.25 | 8.10 |
| Temp. Profile | 7 ; 22 | 7 ; 24 | 7 ; 31 | 8 ; 33 | 2 ; 27 | 4 ; 30 |
| Mole Ratio |  |  |  |  |  |  |
| EDMPA/COS | 0.99 | 0.99 | 1.02 | 0.98 | 0.99 | 0.99 |
| BzCl/COS | 0.94 | 0.94 | 1.00 | 0.97 | 0.94 | 0.94 |
| TEA/COS | 1.88 | 1.88 | 1.01 | na | 1.88 | 2.81 |
| Ratio BzCl/TCB | <0.001 | 0.062 | 0.153 | 0.043 | 0.001 | 0.004 |
| Ratio BzSH/TCB | 0.003 | 0.003 | 0.003 | 0.092 | 0.004 | 0.001 |
| Ratio DTCB/TCB | nd | 0.003 | 0.001 | 0.007 | 0.002 | <0.001 |
| % TCB in Crude Organic | 70.30 | 50.09 | 35.00 | 42.76 [1] | 66.32 | 40.80 |
| % BzCl in Crude Organic | 0.04 | 3.12 | 5.35 | 1.83 | 0.07 | 0.19 |
| % EDMPA in Crude | 1.30 | 4.48 | 2.51 | 1.00 | 1.98 | 2.08 |
| % Solvent in Crude (*) | 27.38 | 41.28 | 50.52 | 43.27 | 30.89 | 56.44 |
| Final Recovered Wt. (G) | 231 |  |  |  | 232.1 | 238 |
| % TCB Purity | 97.5 |  |  |  | 98.35 | 98.37 |
| % Recovered Yield | 85.0 |  |  |  | 86.1 | 88.7 |

|  | Run 25 | Run 26 | Run 27 | Run 28 | Run 29 | Run 32 |
|---|---|---|---|---|---|---|
| Reactor | R5 | glass | glass | glass | glass | glass |
| Solvent | Pyridine | TEA | TEA | TEA | TEA | TEA |
| weight (g) | 237 | 202 | 302 | 302 | 303 | 202 |
| Wt. EDMPA (g) | 121 | 120 | 121 | 121 | 121 | 121 |
| Wt. COS (g) | 64 | 62 | 64 | 64 | 61 | 62 |
| COS addition Time (hrs) | 1.75 | 2.25 | 2.00 | 2.10 | 4.00 | 4.00 |
| COS addition Temp. (°C.) | 2 | 5 | 5 | 9 | 25 | 25 |
| Wt. BzCl (g) | 127 | 127 | 127 | 127 | 127 | 127 |
| When Added | 1 hr after COS addn. | 2.5 hrs after COS addn. | 0.5 hr after COS addn. | initially | initially | initially |
| Time (hrs) | 0.25 | 5.00 | 0.67 |  |  |  |
| Temp. (°C.) | 4 | 7 | 11 |  |  |  |
| Additional Rxn. Time | 4.00 | 5.40 | 4.00 | 5.10 | 2.00 | 3.10 |
| Additional Rxn Temp. | 4 ; 25 | 25 | 37 | 29 | 25 | 25 |
| Additional Solvent | Water | Ether |  |  |  | Water |
| weight (g) | 200 | 200 |  |  |  | 150 |
| When added | after rxn complete | initially |  |  |  | 1 hr after COS addn. |
| Wt. NaOH (g) | (spl from rxn is emulsion) |  | 40 | 40 | 40 |  |
| Wt. Water (g) |  |  | 150 | 200 | 200 |  |
| When Added |  |  | after rxn. complete | after rxn. complete | after rxn. complete |  |
| Time (hrs) |  |  | 0.50 | 0.50 |  |  |
| Temp. (°C.) |  |  | 22 | 22 |  |  |
| Total Reaction Time (hrs) | 7.00 | 10.25 | 7.33 | 7.70 | 6.00 | 7.10 |
| Temp. Profile | 2 ; 25 | 5 ; 25 | 5 ; 37 | 9 ; 29 | 25 | 25 |
| Mole Ratio |  |  |  |  |  |  |
| EDMPA/COS | 0.99 | 1.01 | 0.99 | 0.99 | 1.03 | 1.02 |
| BzCl/COS | 0.94 | 0.97 | 0.94 | 0.94 | 0.98 | 0.97 |
| TEA/COS | na | 1.94 | 2.80 | 2.80 | 2.95 | 1.94 |
| Ratio BzCl/TCB | 0.019 | 0.040 | 0.007 | 0.004 | 0.010 | 0.001 |
| Ratio BzSH/TCB | 0.003 | 0.001 | 0.002 | 0.003 | 0.001 | 0.004 |
| Ratio DTCB/TCB | 0.095 | nd | nd | 0.001 | nd | nd |
| % TCB in Crude Organic | 41.77 | 39.15 | 40.43 | 41.64 | 40.35 | 69.11 |
| % BzCl in Crude Organic | 0.78 | 1.56 | 0.28 | 0.17 | 0.39 | 0.09 |
| % EDMPA in Crude | 10.38 | 2.56 | 1.76 | 2.20 | 2.154 | 1.48 |

TABLE II-continued

Thiolcarbamate Production via COS

| | | | | | | |
|---|---|---|---|---|---|---|
| % Solvent in Crude (*) | 40.20 | 56.31 | 56.97 | 55.37 | 56.61 | 28.35 |
| Final Recovered Wt. (G) | | | 241 | 242 | 249 | 254.4 |
| % TCB Purity | | | 97.95 | 97.74 | 98.08 | 98.2 |
| % Recovered Yield | | | 89.1 | 89.3 | 92.2 | 94.2 |

| | Run 33 | Run 34 | Run 36 | Run 38 | Run 35 | Run 30 |
|---|---|---|---|---|---|---|
| Reactor | glass | glass | glass | glass | glass | glass |
| Solvent | TEA | TEA | TEA | TEA [3] | TBA [5] | TEA |
| weight (g) | 202 | 202 | 400 | 400 | 370 | 303 |
| Wt. EDMPA (g) | 120 | 120 | 240 | 240 | 120 | 121 |
| Wt. COS (g) | 62 | 62 | 122 | 122 [4] | 62 | 62 |
| COS addition Time (hrs) | 2.00 | 1.70 | 3.00 | 4.00 | 2.33 | 3.60 |
| COS addition Temp. (°C.) | 24 | 25 | 22 ; 29 | 23 | 24 | 21 ; 41 |
| Wt. BzCl (g) | 127 | 127 | 255 | 255 | 127 | 93 |
| When Added | initially | initially | initially | initially | initially | initially Butyl Chloride |
| Time (hrs) | | | | | | |
| Temp. (°C.) | | | | | | |
| Additional Rxn. Time | 2.00 | 7.00 | 3.00 | 6.00 | 7.00 | 1.00 |
| Additional Rxn Temp. | 25 | 31 | 25 | 22 ; 29 | 41 | 40 |
| Additional Solvent | | Water | Water | Water | Water | |
| weight (g) | | 100 | 200 | 200 | 100 | |
| When added | | 2 hrs after COS addn. | 2 hrs after COS addn. | 4 hrs after COS addn. | 1.67 hrs after COS addn. | |
| Wt. NaOH (g) | 40 | 40 | 80 | | | 40 |
| Wt. Water (g) | 200 | 100 | 220 | | | 150 |
| When Added | after rxn. Complete | initially | 3 hrs after COS addn. | | | 1 hr after COS addn. |
| Time (hrs) | | | 0.40 | | | 0.50 |
| Temp. (°C.) | | | 25 | | | 38 |
| Total Reaction Time (hrs) | 4.00 | 8.70 | 6.40 | 10.00 | 9.33 | 5.50 |
| Temp. Profile | 25 | 25 ; 31 | 22 ; 29 | 22 ; 29 | 22 ; 41 | 21 ; 41 |
| Mole Ratio | | | | | | |
| EDMPA/COS | 1.01 | 1.01 | 1.03 | 1.03 | 1.01 | 1.02 |
| BzCl/COS | 0.97 | 0.97 | 0.98 | 0.98 | 0.97 | 0.97 |
| TEA/COS | 1.94 | 1.94 | 1.95 | 1.95 | 1.94 | 2.90 |
| Ratio BzCl/TCB | 0.003 | 0.053 | 0.005 | 0.047 | 0.318 | 2.036 |
| Ratio BzSH/TCB | 0.001 | 0.075 | 0.002 | 0.028 | 0.125 | nd |
| Ratio DTCB/TCB | nd | 0.002 | <0.001 | 0.005 | 0.018 | nd |
| % TCB in Crude Organic | 50.86 | 46.61 [2] | 52.74 | 58.57 | 21.20 | 5.98 |
| % BzCl in Crude Organic | 0.17 | 2.46 | 0.30 | 2.75 | 6.75 | 12.19 |
| % EDMPA in Crude | 1.89 | 7.50 | 1.68 | 5.27 | 0.534 | 21.67 |
| % Solvent in Crude (*) | 46.48 | 38.29 | 44.50 | 29.84 | 67.40 | 59.99 |
| Final Recovered Wt. (G) | 253.7 | 233.4 | 516.4 | 447.4 | | |
| % TCB Purity | 98.54 | 87.12 | 98.13 | 96.1 | | |
| % Recovered Yield | 94.4 | 76.7 | 95.6 | | | |

EDMPA = N-ethyl-1,2-dimethylpropylamine; TEA = triethylamine.
BzCl = benzylchloride; BzSH = benzyl mercaptan.
TCB = thiolcarbamate; DTCB = dithiolcarbamate.
na = not applicable; nd = not detected; (*) = did not include water.
[1] Contained 5.36% di-benzyl sulfide.
[2] Product also contained 3.5% benzyl mercaptan and 0.7% di-benzyl sulfide.
[3] 336 grams of recycled TEA from Run 34 + 64 grams fresh TEA.
[4] Used probably not as pure. Crude milky color.
[5] TBA = tri-butyl amine.

The results shown in the above examples clearly demonstrate that the present invention is well adapted to carry out the objects and attain the end and advantages mentioned as well as those inherent therein. While modifications may be made by those skilled in the art, such modifications are encompassed within the spirit of the present invention as defined by the specification and the claims.

That which is claimed:

1. A process comprising reacting a reaction mixture with a hydrocarbyl halide at a temperature in the range of −10° C. to about 80° C. to produce a thiolcarbamate wherein said reaction mixture is in a substantially one-liquid phase medium and comprises carbonyl sulfide, an amine selected from the group consisting of primary amines, and secondary amines or combinations of any two or more thereof, and a solvent comprising a tertiary amine containing no water; and said reaction mixture and hydrocarbyl halide are each present in an amount sufficient to effect the production of a thiolcarbamate.

2. A process according to claim 1 wherein said thiolcarbamate has a formula of R—C(R1)(R1)—S—C(O)—N(R2)(R3) wherein R, each R1, R2, and R3 are each independently selected from the group consisting of hydrogen, alkyl radicals, alkenyl radicals, alkynyl radicals, cycloalkyl radicals, alkoxy radicals, aryl radicals, alkaryl radicals and aralkyl radicals or combinations of any two or more thereof; and each radical has 1 to about 30 carbon atoms.

3. A process according to claim 2 wherein R is phenyl radical.

4. A process according to claim 2 wherein R1 is hydrogen.

5. A process according to claim 2 wherein R2 is ethyl radical.

6. A process according to claim 2 wherein R3 is 1,2-dimethylpropyl radical.

7. A process according to claim 2 wherein R is a phenyl radical, R1 is hydrogen, R2 is ethyl radical, R3 is 1,2-dimethylpropyl radical.

8. A process according to claim 1 wherein said thiolcarbamate is selected from the group consisting of S-ethyl dipropylthiolcarbamate, S-2-chloroallyl diethylthiolcarbamate, S-propyl dipropylthiolcarbamate, S-propyl ethylbutylthiolcarbamate, S-allyl diisoproylthiolcarbamate, S-allyl di-n-propylthiolcarbamate, S-ethyl diisobutylthiolcarbamate, S-ethyl ethylcyclohexylthiolcarbamate, S-benzyl ethyl-1,2-dimethylpropylthiolcarbamate, S-benzyl dipropylthiolcarbamate, S-p-chlorotolyl diethylthiolcarbamate, S-ethyl diethylthiolcarbamate, S-ethyl hexamethylene thiolcarbamate, S-benzyl dimethylthiolcarbamate, S-p-chlorobenzyl diethylthiolcarbamate, S-p-ethylbenzyl dibenzylthiolcarbamate, S-p-iso-propylbenzyl-N-ethyl-N-phenylthiolcarbamate, S-o-methoxybenzyl dimethylthiolcarbamate, S-p-ethoxybenzyl hexamethylenethiolcarbamate, S-p-methylthiobenzyl tetramethylenethiolcarbamate, S-p-ethylthiobenzyl diallylthiolcarbamate, S-p-nitrobenzyl bis(2-hydroxyethyl)thiolcarbamate, S-2,6-dichlorobenzyl dimethylthiolcarbamate, S-p-chloro-o-methoxybenzylbutylmethylthiolcarbamate, S-2-chloro-4-nitrobenzyl pentamethylenethiolcarbamate, S-2-5-dimethylbenzyl dimethylthiolcarbamate and S-3,5-dinitrobenzyl diethylthiolcarbamate or combinations of any two or more thereof.

9. A process according to claim 1 wherein said thiolcarbamate is selected from the group consisting of S-benzyl-ethyl-1,2-dimethylthiolcarbamate and S-benzyl dipropylthiolcarbamate or combinations thereof.

10. A process according to claim 1 wherein said amine is a secondary amine.

11. A process according to claim 1 wherein said amine is selected from the group consisting of N-ethyl-1,2-dimethylpropylamine, N-isobutylallylamine, N-allylmethallylamine, N-propylmethallylamine, N-ethylmethallylamine, N-propargylpropylamine, bis-(2-chloroallyl)amine, trimethylene diamine, ethylene diamine, 2-methoxy-ethylamine, 3-methoxypropylamine, aniline, p-anisidine, p-phenetidine, p-toluidine, 3,4-dichloroaniline, and 2-cyanoethylamine, dimethylamine, diethylamine, dipropylamine, diisopropylamine, dibutylamine, diamylamine, diisobutylamine, diallylamine, bis(2-methoxyethyl)amine, bis(2-phenoxyethyl)amine, bis(2-benzyloxyethyl)amine, piperidine, 5-ethyl-2-methylpiperidine, morpholine, 2,6-dimethylmorpholine, piperazine, 2,5-dimethylpiperazine, pyrrolidine, 4-phenylpiperazine, 2-methylpiperidine, 5-ethyl-3-methylpiperidine, N-(2-chloroallyl)isopropylamine, N-(2-chloroallyl)propylamine, N-ethylaniline, N-allylisopropylamine, N-allylpropylamine, N-allylbutylamine, N-(2-cyanoethyl) isopropylamine, N-(2-chloroallyl)-3-methoxypropylamine, N-ethylcyclohexylamine, N-methylcyclohexylamine, N-ethyl-isoamylamine, N-methylbutylamine, N-ethylbutylamine, N-(2-chloroallyl)allylamine, N-(3-chloroallyl)allylamine, N-(3-chloroallyl)ethylamine and N-(3-chloroallyl)propylamine or combinations of any two or more thereof.

12. A process according to claim 1 wherein said amine is selected from the group consisting of N-ethyl-1,2-dimethylpropylamine and dipropylamine or combinations thereof.

13. A process according to claim 1 wherein said hydrocarbyl halide has a formula of R—C(R1)(R1)—X wherein R and each R1 are each independently selected from the group consisting of hydrogen, alkyl radicals, alkenyl radicals, alkynyl radicals, cycloalkyl radicals, alkoxy radicals, aryl radicals, alkaryl radicals and aralkyl radicals or combinations of any two or more thereof; each radical has 1 to about 30 carbon atoms; and X is a halide radical.

14. A process according to claim 1 wherein said hydrocarbyl halide is selected from the group consisting of benzyl chloride, benzyl bromide, benzyl iodide, ally chloride, allyl bromide, allyl iodide, 2-chloroallyl chloride, 2-chloroallyl bromide, methallyl chloride, methallyl bromide, fluorobenzyl chlorides, fluorobenzyl bromides, chlorobenzyl chlorides, chlorobenzyl bromides, bromobenzyl chlorides, bromobenzyl bromides, iodobenzyl chlorides, methylbenzyl chlorides, methylbenzyl bromides, nitrobenzyl chlorides, nitrobenzyl bromides, cyanobenzyl chlorides, cyanobenzyl bromides, 4-ethylbenzyl chloride, 4-(isopropyl)benzyl chloride, 4-(isopropyl)benzyl chloride, 2-methoxybenzyl chloride, 3-ethoxybenzyl bromide, 4-(isopropoxy)benzyl chloride, 4-methylthiobenzyl chloride, 4-ethylthiobenzyl chloride, dichlorobenzyl chlorides, 4-chloro-2-methoxybenzyl chloride, 2-chloro-4-nitrobenzyl chloride, 2,5-dimethylbenzyl chloride, 4-methyl-3-nitrobenzyl chloride and 3,5-dinitrobenzyl chloride or combinations of any two or more thereof.

15. A process according to claim 1 wherein said hydrocarbyl halide is benzyl chloride.

16. A process according to claim 1 wherein said tertiary amine is selected from the group consisting of trimethylamine, triethylamine, tri-n-propylamine, tri-n-butylamine, triisopropylamine, methyl-diethylamine, methyl-di-n-propylamine, methyl-diisopropylamine, ethyl-dimethylamine, ethyl-di-n-propylamine, ethyl-diisopropylamine, tri-t-butylamine and amyl-diisoamylamine, or combinations of any two or more thereof.

17. A process according to claim 1 wherein said tertiary amine is triethylamine.

18. A process according to claim 1 wherein said reaction mixture further comprises a metal hydroxide.

19. A process according to claim 18 wherein said metal hydroxide is selected from the group consisting of alkali metal hydroxides and alkaline earth metal hydroxides or combinations of any two or more thereof.

20. A process according to claim 1 wherein said mixture is contacted with a metal hydroxide.

21. A process according to claim 20 wherein said metal hydroxide is selected from the group consisting of alkali metal hydroxides and alkaline earth metal hydroxides or combinations of any two or more thereof.

22. A process according to claim 20 wherein said metal hydroxide is sodium hydroxide.

23. A process for producing a thiolcarbamate comprising the steps of: (1) forming a reaction mixture; and (2) reacting said reaction mixture with a hydrocarbyl halide at a temperature in the range of −10° C. to about 80° C. to produce a thiolcarbamate wherein:

said reaction mixture consists essentially of carbonyl sulfide, an amine selected from primary amines and secondary amines or combinations of any two or more thereof, and a solvent comprising a tertiary amine containing no water; and said reaction mixture and hydrocarbyl halide are each present in an amount sufficient to effect the production of a thiolcarbamate;

said thiolcarbamate has a formula of R—C(R1)(R1)—S—C(O)—N(R2)(R3) wherein R, R1, R2, and R3 are each independently selected from the group consisting of hydrogen, alkyl radicals, alkenyl radicals, alkynyl radicals, cycloalkyl radicals, alkoxy radicals, aryl radicals, alkaryl radicals and aralkyl radicals or combinations of any two or more thereof; and each radical has 1 to about 30 carbon atoms;

said secondary amine is selected from the group consisting of N-ethyl-1,2-dimethylpropylamine, N-isobutylallylamine, N-allylmethallylamine, N-propylmethallylamine, N-ethylmethallylamine, N-propargylpropylamine, bis-(2-chloroethyl)amine, bis-(2-chloropropyl)amine, trimethylene diamine, ethylene diamine, N,N-dimethyl hydrazine, 2-methoxyethylamine, 3-methoxypropylamine, aniline, p-anisidine, p-phenetidine, p-toluidine, 3,4-dichloroaniline, and 2-cyanoethylamine, dimethylamine, diethylamine, dipropylamine, diisopropylamine, dibutylamine, diamylamine, diisobutylamine, diallylamine, bis(2-methoxyethyl)amine, bis(2-phenoxyethyl)amine, bis(2-benzyloxyethyl)amine, piperidine, 5-ethyl-2-methylpiperidine, morpholine, 2,6-dimethylmorpholine, piperazine, 2,5-dimethylpiperazine, pyrrolidine, 4-phenylpiperazine, 2-methylpiperidine, 5-ethyl-3-methylpiperidine, N-(2-chloroallyl)isopropylamine, N-(2-chloroallyl)propylamine, N-ethylaniline, N-allylisopropylamine, N-allylpropylamine, N-allylbutylamine, N-(2-cyanoethyl)isopropylamine, N-(2-chloroallyl)-3-methoxypropylamine, N-ethylcyclohexylamine, N-methylcyclohexylamine, N-ethylisoamylamine, N-methylbutylamine, N-ethylbutylamine, N-(2-chloroallyl)allylamine, N-(3-chloroallyl)allylamine, N-(3-chloroallyl)ethylamine and N-(3-chloroallyl)propylamine or combinations of any two or more thereof;

said hydrocarbyl halide has a formula of R—C(R1)(R1)—X wherein R and each R1 are each independently selected from the group consisting of hydrogen, alkyl radicals, alkenyl radicals, alkynyl radicals, cycloalkyl radicals, alkoxy radicals, aryl radicals and alkaryl radicals, aralkyl radicals or combinations of any two or more thereof; each radical has 1 to about 30 carbon atoms; and X is a halide radical; and said tertiary amine is selected from the group consisting of trimethylamine, triethylamine, tri-n-propylamine, tri-n-butylamine, triisopropylamine, methyl-diethylamine, methyl-di-n-propylamine, methyl-diisopropylamine, ethyl-dimethylamine, ethyl-di-n-propylamine, ethyl-diisopropylamine, tri-t-butylamine and amyl-diisoamylamine or combinations of any two or more thereof.

24. A process according to claim 23 wherein:

R is phenyl radical, R1 is hydrogen, R2 is ethyl radical, R3 is 1,2-dimethylpropyl radical;

said thiolcarbamate is selected from the group consisting of S-benzyl-ethyl-1,2-dimethylthiolcarbamate and S-benzyl dipropylthiolcarbamate or combinations thereof;

said amine is selected from the group consisting of N-ethyl-1,2-dimethylpropylamine, and dipropylamine or combinations thereof;

said hydrocarbyl halide is benzyl chloride; and said tertiary amine is triethylamine.

25. A process according to claim 23 wherein said mixture is contacted with a metal hydroxide.

26. A process according to claim 25 wherein said metal hydroxide is sodium hydroxide.

27. A process for producing a thiolcarbamate comprising the steps of: (1) forming a reaction mixture consisting essentially of carbonyl sulfide, a secondary amine, and triethylamine containing no water; (2) reacting said reaction mixture with benzyl chloride and (3) further reacting mixture with a metal hydroxide; wherein said thiolcarbamate is selected from the group consisting of S-benzyl ethyldimethylthiolcarbamate and S-benzyl dipropylamine or combinations thereof; said secondary amine is selected from the group consisting of N-ethyl-1,2-dimethylpropylamine and dipropylamine or combinations thereof; said metal hydroxide is selected from the group consisting of alkali metal hydroxides and alkaline earth metal hydroxides or combinations of any two or more thereof; the molar ratio of said triethylamine to carbonyl sulfide is in the range of from 1.5:1 to about 20:1 and said process is carried out at a temperature in the range of from about −10° to about 60° C.

28. A process according to claim 1 wherein said carbonyl sulfide is prepared in-situ by combining carbon monoxide and sulfur in said reaction mixture.

29. A process according to claim 23 wherein said carbonyl sulfide is prepared in-situ by combining carbon monoxide and sulfur in said reaction mixture.

30. A process according to claim 27 wherein said carbonyl sulfide is prepared in-situ by combining carbon monoxide and sulfur in said reaction mixture.

31. A process according to claim 28 wherein said mixture is contacted with a metal hydroxide.

32. A process according to claim 31 wherein said metal hydroxide is sodium hydroxide.

33. A process according to claim 27 wherein said secondary amine is N-ethyl-1,2-dimethylpropylamine and the molar ratio of N-ethyl-1,2-dimethylpropylamine to carbonyl sulfide is about 1:1 and the molar ratio of said solvent to carbonyl sulfide is in the range of from 1.5:1 to 3:1.

34. A process according to claim 1 wherein said process is carried out as one-pot reaction.

35. A process according to claim 22 wherein said amine is N-ethyl-1,2-dimethylpropylamine.

36. A process according to claim 26 wherein said amine is N-ethyl-1,2-dimethylpropylamine.

37. A process according to claim 32 wherein said amine is N-ethyl-1,2-dimethylpropylamine.

\* \* \* \* \*